United States Patent [19]

Ichitsuka et al.

[11] Patent Number: 5,240,659

[45] Date of Patent: Aug. 31, 1993

[54] PROCESS FOR PRODUCING SHAPED ARTICLE OF ORIENTED CALCIUM PHOSPHATE TYPE COMPOUND

[75] Inventors: Takeshi Ichitsuka; Tetsuro Ogawa; Masaya Sumita; Akihiko Yokoo, all of Tokyo, Japan

[73] Assignee: Asahi Kogaku K.K., Tokyo, Japan

[21] Appl. No.: 857,638

[22] Filed: Mar. 24, 1992

Related U.S. Application Data

[63] Continuation of Ser. No. 407,009, Sep. 14, 1989, Pat. No. 5,134,009.

[30] Foreign Application Priority Data

Sep. 15, 1988 [JP] Japan ............................ 63-230570

[51] Int. Cl.$^5$ .................. C04B 35/64; B29C 67/00
[52] U.S. Cl. ........................... 264/63; 264/108; 264/109; 264/125
[58] Field of Search ............. 264/16, 56, 63, 108, 264/125, 109

[56] References Cited

U.S. PATENT DOCUMENTS

| | | | |
|---|---|---|---|
| 3,522,338 | 7/1970 | Kass et al. | 264/125 |
| 4,699,742 | 10/1987 | Nakamura et al. | 264/56 |
| 4,942,151 | 7/1990 | Capone et al. | 505/1 |

*Primary Examiner*—Mary Lynn Theisen
*Attorney, Agent, or Firm*—Sughrue, Mion, Zinn, Macpeak & Seas

[57] ABSTRACT

An oriented shaped article of a calcium phosphate type compound is disclosed, in which at least two crystallographic axes of the primary particles of which the shaped article is composed each is oriented in one direction, respectively, in at least the surface of said article. A sinter of the oriented shaped article and a processes for producing the article and the sinter are also disclosed.

16 Claims, 9 Drawing Sheets

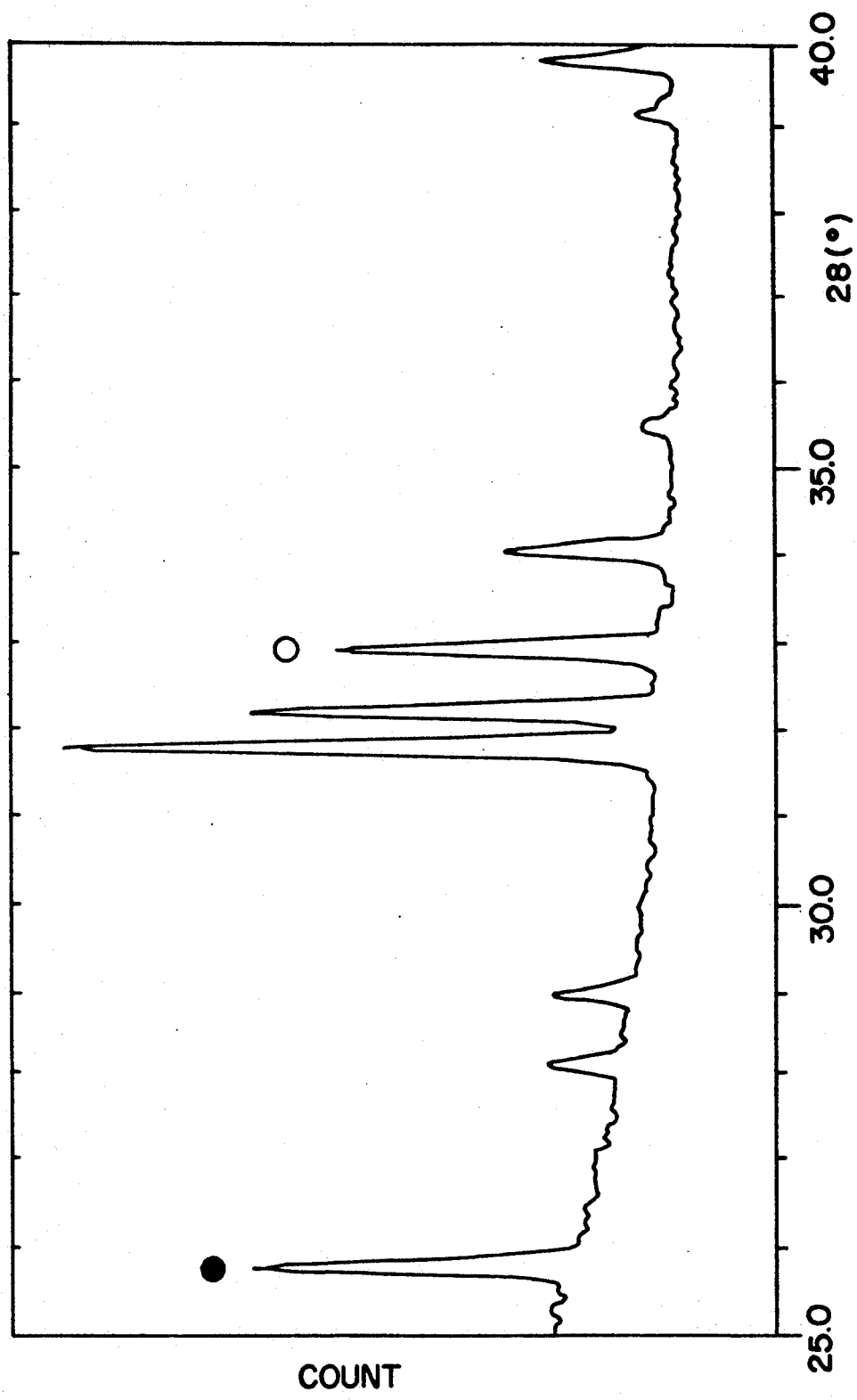

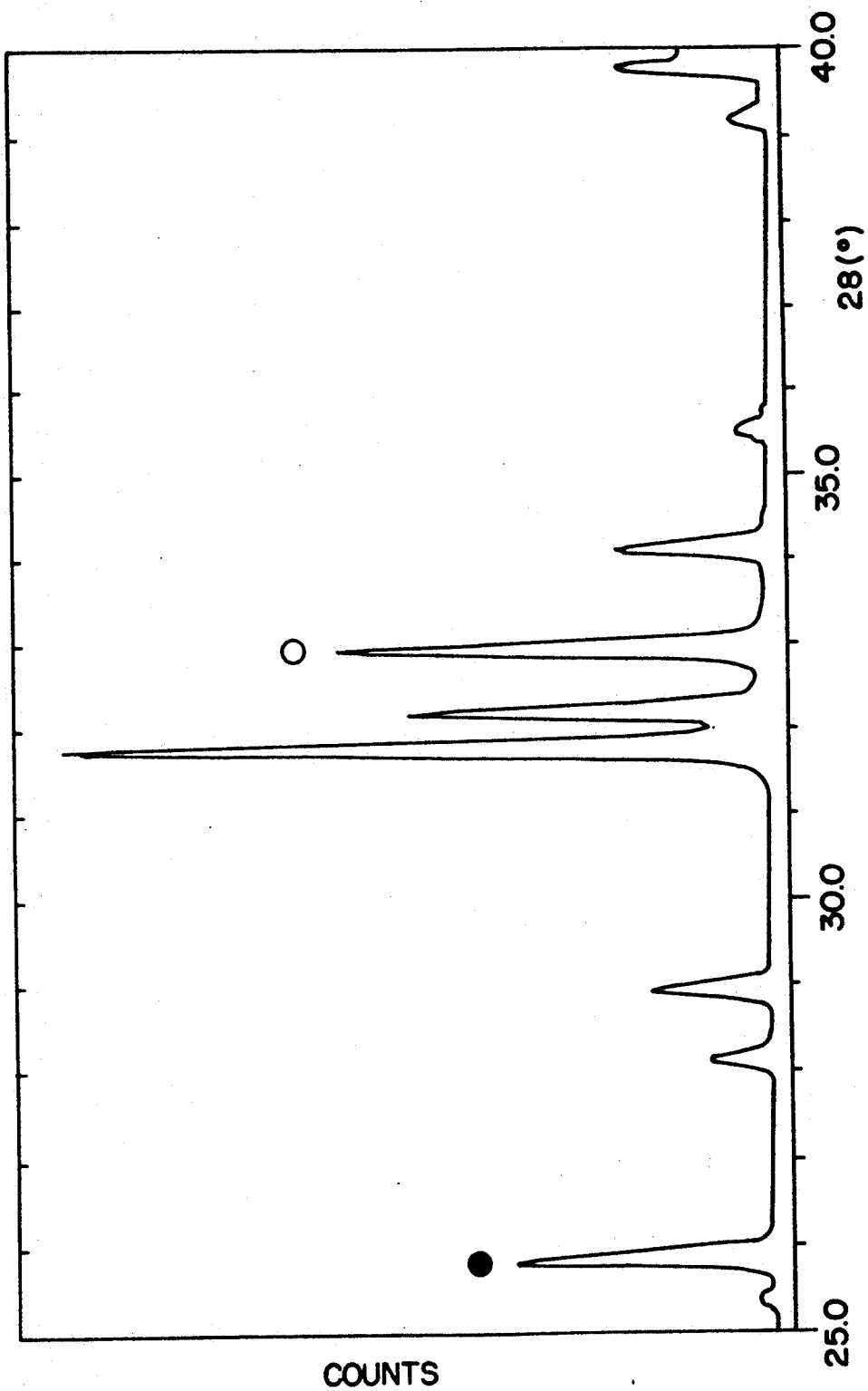

PROCESS FOR PRODUCING SHAPED ARTICLE OF ORIENTED CALCIUM PHOSPHATE TYPE COMPOUND

This is a continuation of application Ser. No. 07/407,009, filed Sep. 14, 1989, now U.S. Pat. No. 5,134,009.

FIELD OF THE INVENTION

The present invention relates to shaped articles of calcium phosphate type compounds useful as biomaterials (e.g., artificial teeth and bones) or as materials for humidity sensors, filters or IC substrates. The present invention also relates to sinters of these shaped articles and processes for producing the shaped articles and the sinters.

BACKGROUND OF THE INVENTION

Due to their high biocompatibility, calcium phosphate type ceramics have conventionally been used as biomaterials such as artificial tooth roots and bones. Because the crystal particles (primary particles) of these ceramics are unoriented and these ceramics are unoriented polycrystalline bodies, the mechanical properties of these ceramics are isotropic. When these ceramics are placed under stress, the propagation of a fracture will travel over the shortest distance irrespective of the direction in which the stress is applied and the surface energy for a fracture becomes so small that it will eventually cause a reduction in the fracture toughness of a shaped article of these ceramics and hence sinters thereof. Attempts have been made to increase the strength of these ceramics by sintering them for high density after performing a suitable treatment such as HIP (hot isotactic press), but no success has been achieved in improving their fracture toughness (as described, e.g., in *Preprints of Annual Meeting of the Ceramics Society of Japan* 1984, 3G10, pp. 939, published on May 14, 1984).

Hydroxyapatite which is in the class of calcium phosphate type compounds has ionic conductivity and research has been undertaken to study its use as an electronic material in devices such as humidity sensors. However, conventional hydroxyapatite ceramics are also isotropic with respect to electrical properties, and conduction ions in the ceramics are diffused at grain boundaries, making it impossible to provide satisfactory conductivity to the ceramics (As described, e.g., in *Preprints of 2nd Apatite Meeting*, pp. 22, published on Dec. 1, 1986).

In order to exploit the above various properties of calcium phosphate type ceramics in an advantageous way, it is necessary that shaped articles or sinters thereof have anisotropy. The ideal method for meeting this need would be to use single crystals of these ceramics. However, it is generally difficult to prepare large single crystals of calcium phosphate, and, in fact, no report has been published that describes success in preparing large single crystals of calcium phosphate.

In order to attain anisotropy for various properties of shaped articles and sinters, it is nessesary that at least two crystallographic axes or at least two crystal faces each must be oriented in one direction, respectively. For example, in tubular bones of animals, the c axis of apatite crystals in the bone is oriented in the direction parallel to the longitudinal direction of the bone, and the a axis thereof is oriented in the direction perpendicular to the longitudinal direction of the bone, by which the anisotropy of the mechanical properties is attained.

Hydroxyapatite sinters in which one crystal face of the crystalline particles is oriented by hot-pressing has been reported in *Preprints of Annual Meeting of the Ceramic Society of Japan* 1984, A-72, pp. 511, published on May 14, 1984. In this method, because tabular (plate-like) crystals are used, the (h00) plane is oriented in the pressing direction, but there is no research whether other planes (such as the (00l) plane) are oriented in one direction. Therefore, it is unknown whether sinters having anisotropy for mechanical properties are obtained by this method.

SUMMARY OF THE INVENTION

The present inventors therefore conducted intensive studies in order to develop calcium phosphate type ceramics in which the crystal grains (i.e., the primary particles) are oriented in one direction and thus succeeded in reaching the present invention.

One object of the present invention is to provide a shaped article of an oriented calcium phosphate type compound.

Another object of the present invention is to provide a sinter of a shaped article of an oriented calcium phosphate type compound.

A further object of the present invention is to provide processes for producing such a shaped article and the sinter.

Other objects and effects of the present invention will be more apparent from the following description.

The present invention provides a shaped article of a calcium phosphate type compound in which at least two crystallographic axes of the primary particles which make up the shaped article each is oriented in one direction, respectively, in at least the surface of the article. Such orientation can be throughout the entire article.

Such an oriented shaped article of a phosphate type compound can be produced by a process which comprises mixing an organic binder and water or an organic solvent with a powdered calcium phosphate type compound comprising rod-shaped crystal grains extending in the direction of one crystallographic axis thereof, kneading the mixed components, and extruding the resulting clay-like composition in a specified direction to shape the composition.

The present invention also provides an oriented sinter of a calcium phosphate type compound in which at least two crystallographic axes of the primary particles which make up the sinter each is oriented in one direction, respectively, in at least the surface of the sinter. The entire sinter can be oriented.

Such an oriented sinter of a calcium phosphate type compound can be produced by a process comprising mixing an organic binder and water or an organic solvent with a powdered calcium phosphate type compound comprising rod-shaped crystal grains extending in the direction of one crystallographic axis, kneading the mixed components, extruding the resulting clay-like composition in a specified direction to shape the composition, thermally decomposing the organic binder, and firing the shaped article at a temperature of from 900° to 1,400° C.

BRIEF DESCRIPTION OF THE DRAWINGS

FIG. 8 is an X-ray diffraction scan for the plane perpendicular to the molding direction of the shaped article prepared in Example 4.

FIG. 9 is an X-ray diffraction scan for the shaped article prepared in Example 4 after it was pulverized.

DETAILED DESCRIPTION OF THE INVENTION

Figure 1:
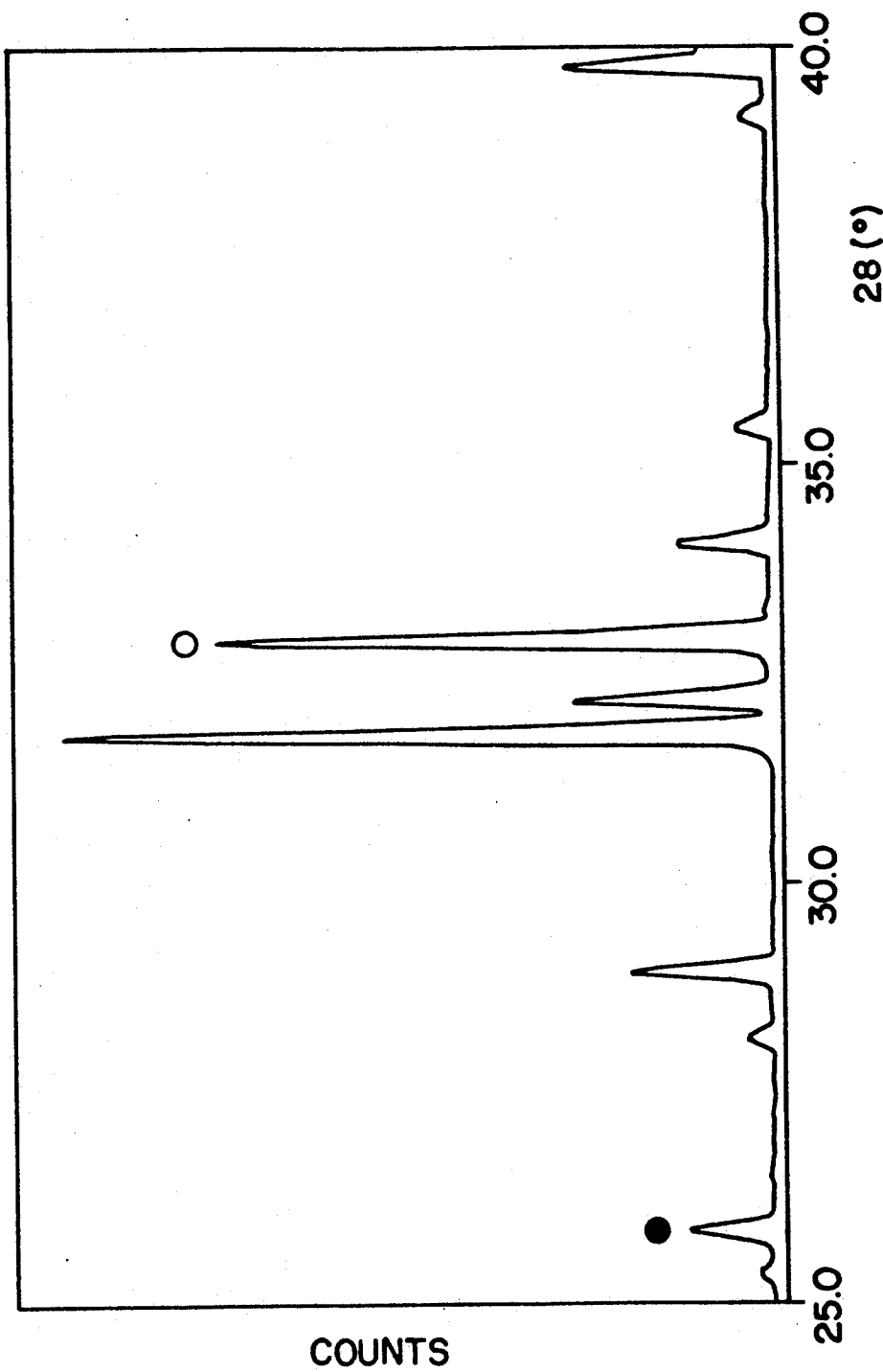
FIG. 1 is an X-ray diffraction scan for the shaped article prepared in Example 1.

Examples of the calcium phosphate type compound of the present invention include hydroxyapatite, fluoroapatite, chloroapatite and tricalcium phosphate.

A commonly employed method for orienting grains in the direction of a certain crystallographic axis is by utilizing the electric or magnetic polarity of the grains. This method, however, is not highly effective in orienting the crystals of calcium phosphate type compounds because their polarity is rather low.

If calcium phosphate type compounds are synthesized by a wet method under properly selected conditions, it is possible to prepare rod-like crystal grains that are elongate in the direction of the c-axis as described in *J. Am. Chem. Soc.*, Oct. 25, 1967, pp. 5535–5541. For instance, such grains can be synthesized by mixing a calcium compound with a phosphoric acid compound, the pH of the reaction solution being adjusted to either neutral or alkaline with the temperature held in the range of from 10° to 100° C. The ratio of the long axis to the short axis of the rod-like grains is preferably 1.1 or more, more preferably 1.5 or more, and particularly preferably 2.0 or more.

The present inventors found that when the thus prepared rod-like grains were placed in a flowing fluid, they could be oriented in the direction in which the fluid was flowing.

These rod-shaped crystal grains (primary particles) can form secondary particles when the slurry is dried. The secondary particles as such will not be oriented if they are subjected to shaping, so it is necessary to pulverize the secondary particles into primary particles by a suitable method such as a jet-mill attrition process and a supersonic mill attrition process.

The secondary particles of a calcium phosphate type compound can be pulverized into primary particles when they are mixed with an organic binder and water or an organic solvent. If the slurry is not dried but is subjected to filtration, no secondary particles will form and the synthesized crystal grains may be directly used without being pulverized.

Therefore, in accordance with the present invention, the rod-shaped crystal grains of a calcium phosphate type compound are used as a starting powder, which is mixed with suitable amounts of a heat-decomposable organic binder and water or an organic solvent, as well as optionally with other additives such as a dispersant and a plasticizer. The ingredients are kneaded and the resulting clay-like composition is extruded to shape the same.

Various kinds of heat-decomposable organic binders and dispersants may be used without any particular limitation and illustrative examples include organic high-molecular weight compounds and sublimable solid substances. Specific examples of the binders include methyl cellulose, butyl methacrylate, ethylene-vinyl acetate copolymers and pullulan. Illustrative organic solvents include various kinds of alcohols, hydrocarbons, halogenated hydrocarbons, ethers, ketones and esters.

Any shaping method can be used as long as it permits the composition to be given the desired shape as it is extruded in a specified direction. Illustrative examples are extrusion molding, extrusion spinning and doctor blading as well as injection molding. If injection molding is used, the desired orientation can be achieved by shaping the composition with a mold having a structure which permits the molding composition which is being fed to flow in a specified direction. In the doctor blading, the grains being shaped are subjected to a smaller force than in other shaping methods. It is therefore necessary that the dispersability of the ceramic particles in the composition be increased to make it less viscous. As the spinning method, those described in JP-A-61-106166 can be employed.

In the case where extrusion molding is employed, the molding pressure is preferably from 0.2 to 500 kg/cm$^2$. In the case where injection molding is employed, the molding pressure is preferably from 500 to 3,000 kg/cm$^2$.

The shaped article, in which the crystallographic axes are oriented only in the surface of the article, can be prepared, e.g., by extrusion molding in which the composition is extruded at a relatively low pressure through a die having a large diameter. By using such molding conditions, the inside part of the shaped article becomes less oriented because of a small stress during the molding. The sinter, in which the crystallographic axes are oriented only in the surface of the sinter, can be prepared by sintering such a shaped article.

The resulting shaped article is heated to decompose and thereby remove the organic binder and other organic substances by a conventional method. Subsequently, the article is fired by a conventional method, e.g., at a temperature of from 900° to 1,400° C. to make a sinter that is dense and that has satisfactory strength.

The following examples are provided for the purpose of further illustrating the present invention but are in no way to be taken as limiting. In the examples, all "parts" and "percentages" are on a weight basis unless otherwise noted.

EXAMPLE 1

A slurry of hydroxyapatite synthesized by a conventional wet method (as described in *J. Am. Chem. Soc.*, Oct. 25, 1967, pp. 5535–5541) was spray-dried to make a powder having an average particle size of about 7 μm. Observation under a scanning electron microscope showed that the powder was composed of spherical secondary particles which were dense agglomerations of elongate primary grains having a width of from 200 to 500 Å and length of about 1,000 Å. These particles were calcined at 700° C. for 4 hours and pulverized with a supersonic mill (product of Nippon Pneumatic Co., Ltd.) to obtain a fine powder having an average particle size of about 1 μm. This fine powder (feed powder) was used as a starting material for the next shaping step.

The fine powder prepared above (100 parts), water (45 parts), butyl alcohol (5 parts), methyl cellulose (7 parts), a wax (paraffin) emulsion (40% solid content; 1.5 parts) and a stearic acid emulsion (20% solid content; 1.5 parts) were mixed and kneaded to form a homogeneous clay-like composition. By mixing and kneading, the fine powder was completely pulverized into primary particles. The composition was extrusion-molded to form a cylinder, a hollow cylinder and a honeycomb. The molding pressure depended on the shape of the articles, and was about 30 kg/cm² for the cylinder, about 50 kg/cm² for the hollow cylinder, or about 75 kg/cm² for the honeycomb. The shaped articles were dried at room temperature, heated in a degreasing furnace at 700° C. to decompose and remove any residual organic substance in the article, and sintered at 1,200° C. in a box-shaped electric furnace.

Figure 2:
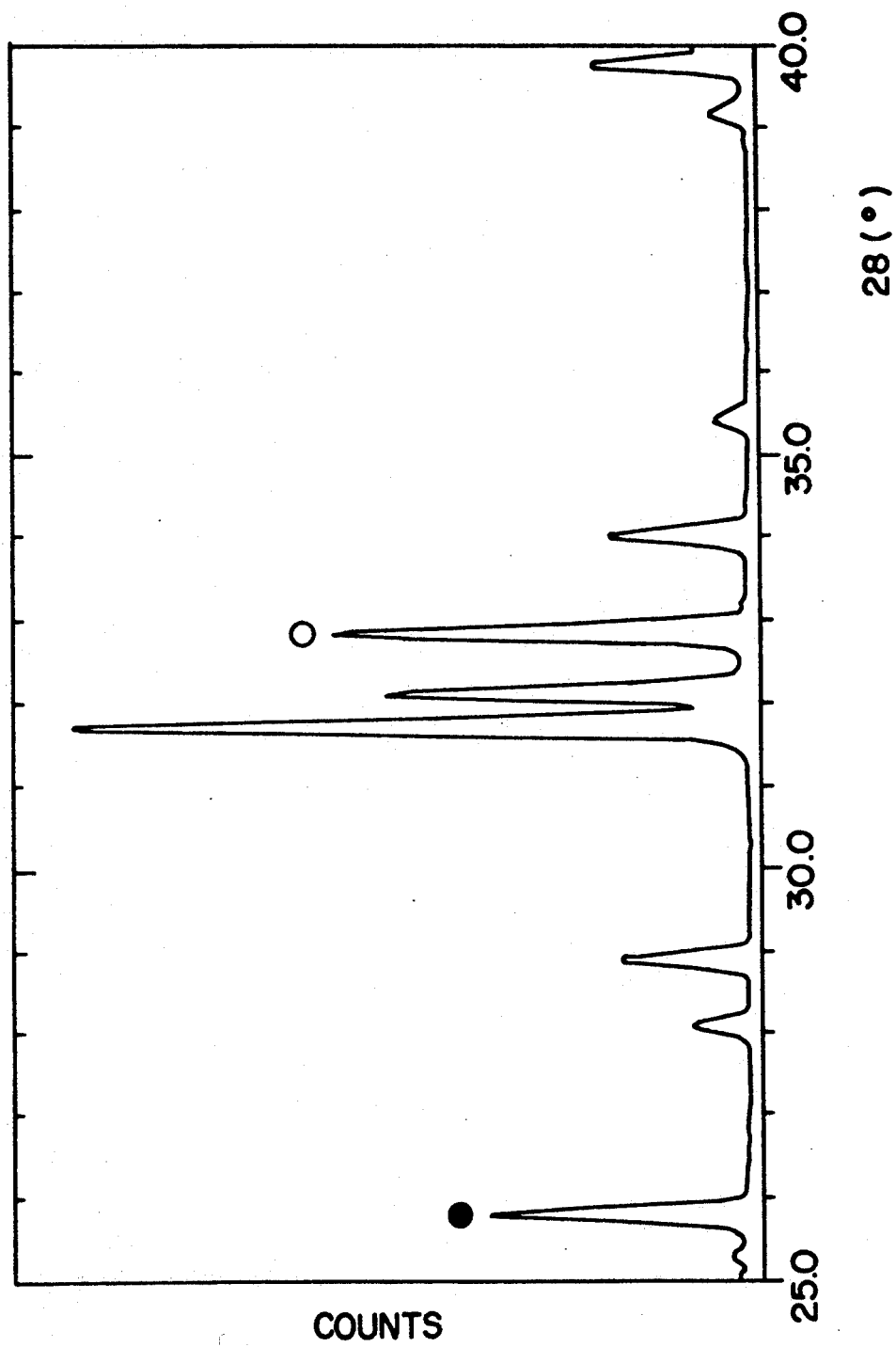
FIG. 2 is an X-ray diffraction scan for the shaped article prepared in Example 1 after it was pulverized.

The result of X-ray diffractiometry for the surface of each shaped article is shown in FIG. 1, and the result of X-ray diffractiometry for each article after it was pulverized in a mortar is shown in FIG. 2. In each figure, the open circle represents the diffraction peak for the (300) face and the solid circle represents the diffraction peak for the (002) face. X-ray diffractiometry was performed at 40 kV and 100 mA using CuKα. When the surfaces of the shaped articles were directly measured, the diffraction intensity from the (300) face was higher than when the pulverized samples were measured. On the other hand, the diffraction intensity from the (002) face was lower in the intact shaped samples than in the pulverized samples. This shows the presence of orientation in the shaped articles.

The "degree of orientation" of hydroxyapatite as defined below is shown in Table 1 for each sample. As one can see from Table 1, the sinters of the shaped articles prepared in Example 1 had the c-axis of the primary particles oriented in the direction of extrusion. However, the pulverized products of these sinters showed no appreciable orientation and the relative intensities of individual diffraction lines were in accord with the data of ASTM 24-33.

The "degree of orientation" of hydroxyapatite as used herein is defined by $$\frac{(I_{(300)}/I_{(002)})}{1.5} - 1,$$

wherein $I_{(300)}$ is the diffraction intensity from the (300) face of a sample, and $I_{(002)}$ is the diffraction intensity from the (002) face of the sample. The ASTM value for $I_{(300)}/I_{(002)}$ is 1.5.

EXAMPLE 2

Using the powder feed prepared in Example 1, a composition of the following recipe was produced:

| Composition | Amount (parts) |
|---|---|
| Fine powder prepared in Example 1 | 100 |
| Butyl methacrylate | 12.5 |
| Ethylene-Vinyl acetate copolymer | 9 |
| Wax emulsion | 9.5 |
| Dibutyl phthalate | 3 |

-continued

| Composition | Amount (parts) |
|---|---|
| Stearic acid | 1.5 |

The composition thus produced was kneaded as in Example 1 and was injection molded at an injection pressure of 1,500 kg/cm² in a plate mold such that the composition flowed in the direction parallel to the plate mold to produce an article in a plate form.

The shaped article was placed in a degreasing furnace and heated while increasing the temperature at a rate of 1.5° C./hour, followed by holding at 700° C. for 10 hours. After degreasing, the article was sintered at 1,200° C.

Figure 3:
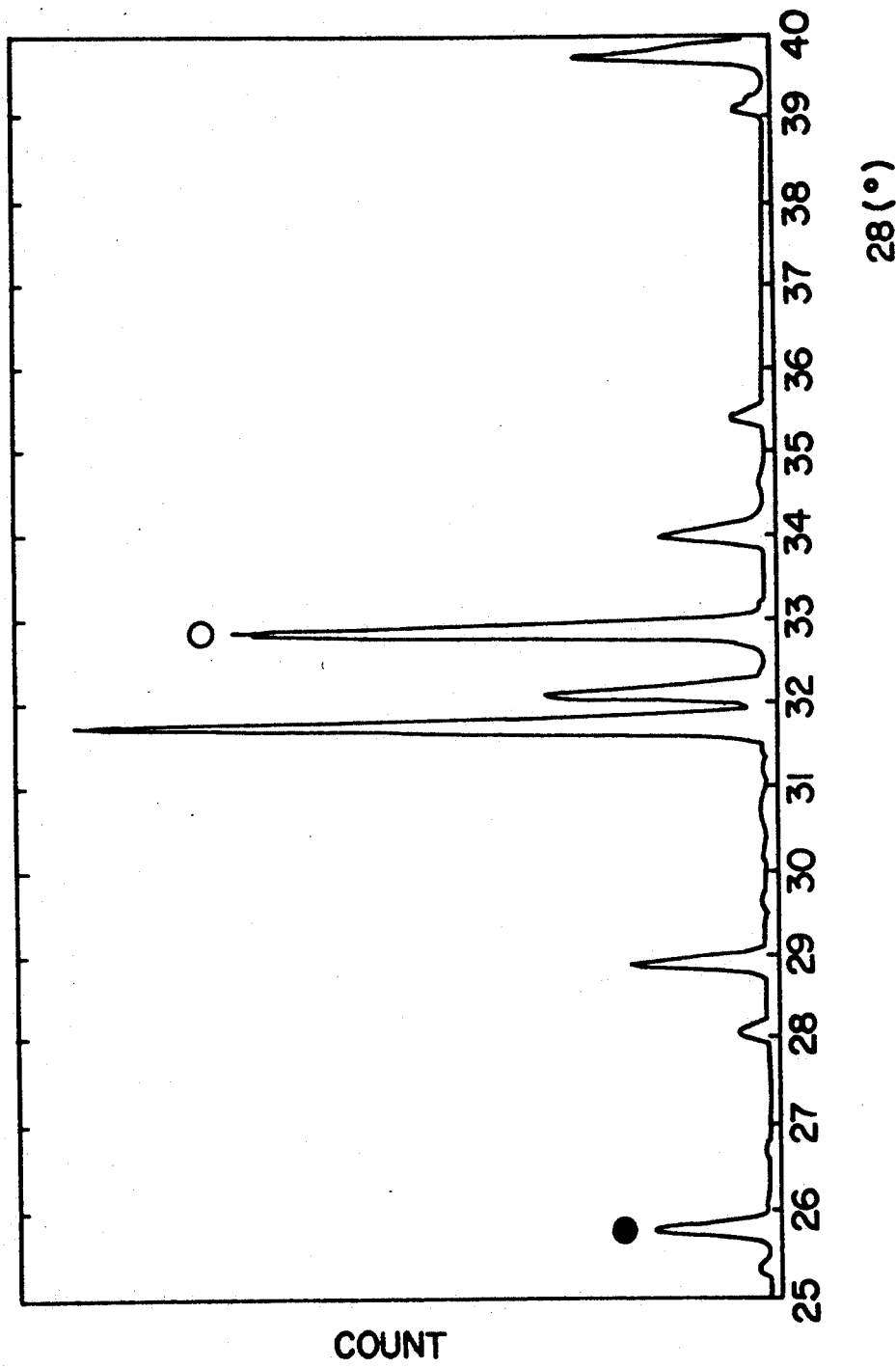
FIG. 3 is an X-ray diffraction scan for the shaped article prepared in Example 2.
Figure 4:
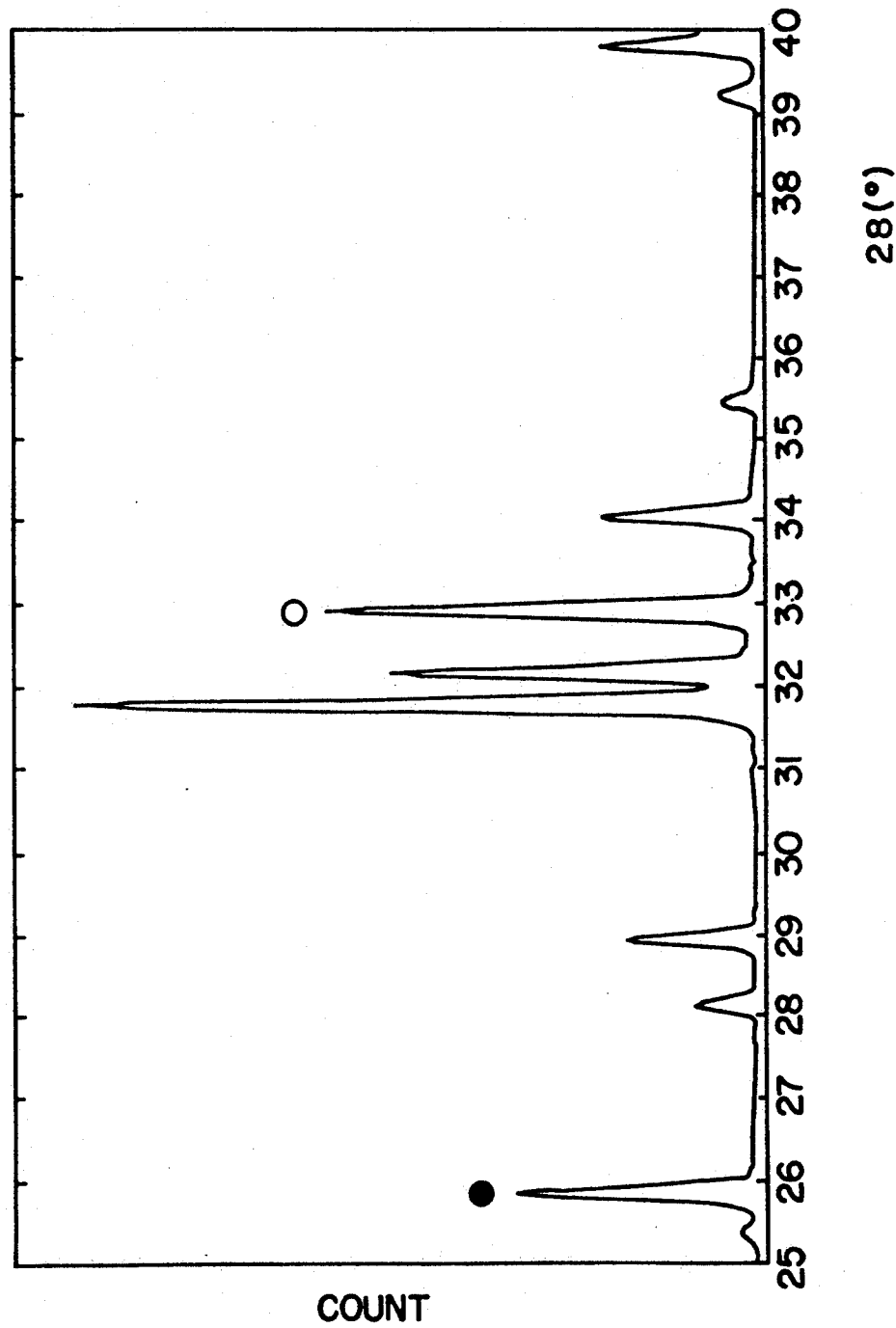
FIG. 4 is an X-ray diffraction scan for the shaped article prepared in Example 2 after it was pulverized.

The result of X-ray diffractiometry on the shaped article is shown in FIG. 3 and the result of X-ray diffractiometry for the pulverized product of the shaped article is shown in FIG. 4. As is clear from these results and from the data shown in Table 1, the shaped article produced in Example 2 had grain orientation as in Example 1.

EXAMPLE 3

A slurry containing 4% hydroxyapatite particles (based on total slurry weight) with a width of from 200 to 500 and a length of about 1,000 Å was obtained by a conventional wet method of synthesis (as described in *J. Am. Chem. Soc.*, Oct. 25, 1967, pp. 5535–5541). The slurry was concentrated by filtration, and the following composition was obtained.

| Composition | Amount |
|---|---|
| Hydroxyapatite | 40% |
| Water | 50% |
| Pullulan | 10% |

The composition containing the thus synthesized rod-shaped crystals of hydroxyapatite, a binder and water was spun by extrusion through an air nozzle (diameter: 0.3 mm) at an air pressure of 900 mmH₂O according to JP-A-61-106166, and dried with hot air at 300° C. to form a gauze-like shaped article. The dried article was sintered at 1,100° C. for 4 hours and subjected to X-ray diffractiometry to check for the occurrence of orientation. When an unpulverized sample of the gauze-like article was loaded in a glass sample holder, grain orientation was observed in the same manner as in Examples 1 and 2.

Figure 5:
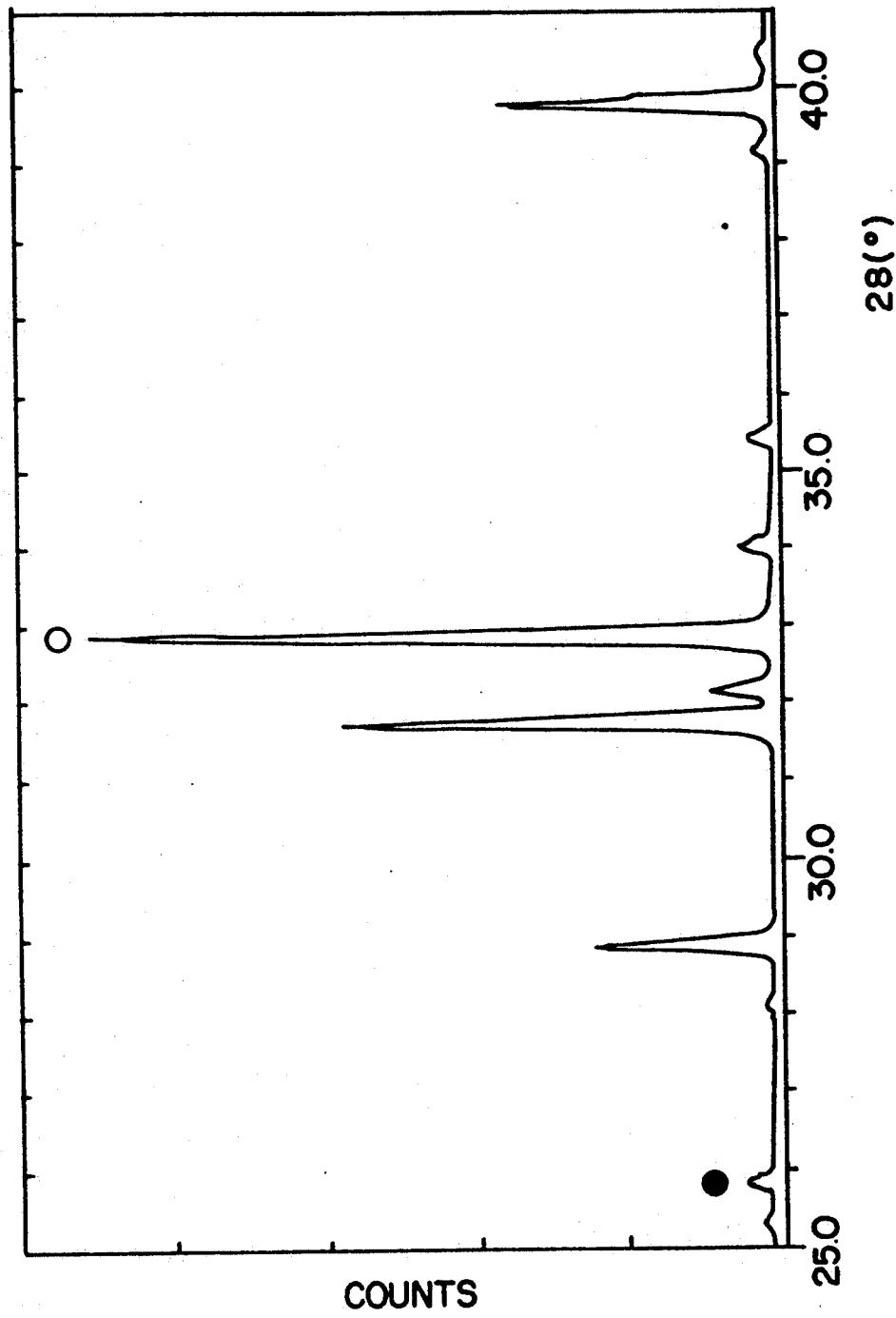
FIG. 5 is an X-ray diffraction scan for the shaped article prepared in Example 3.
Figure 6:
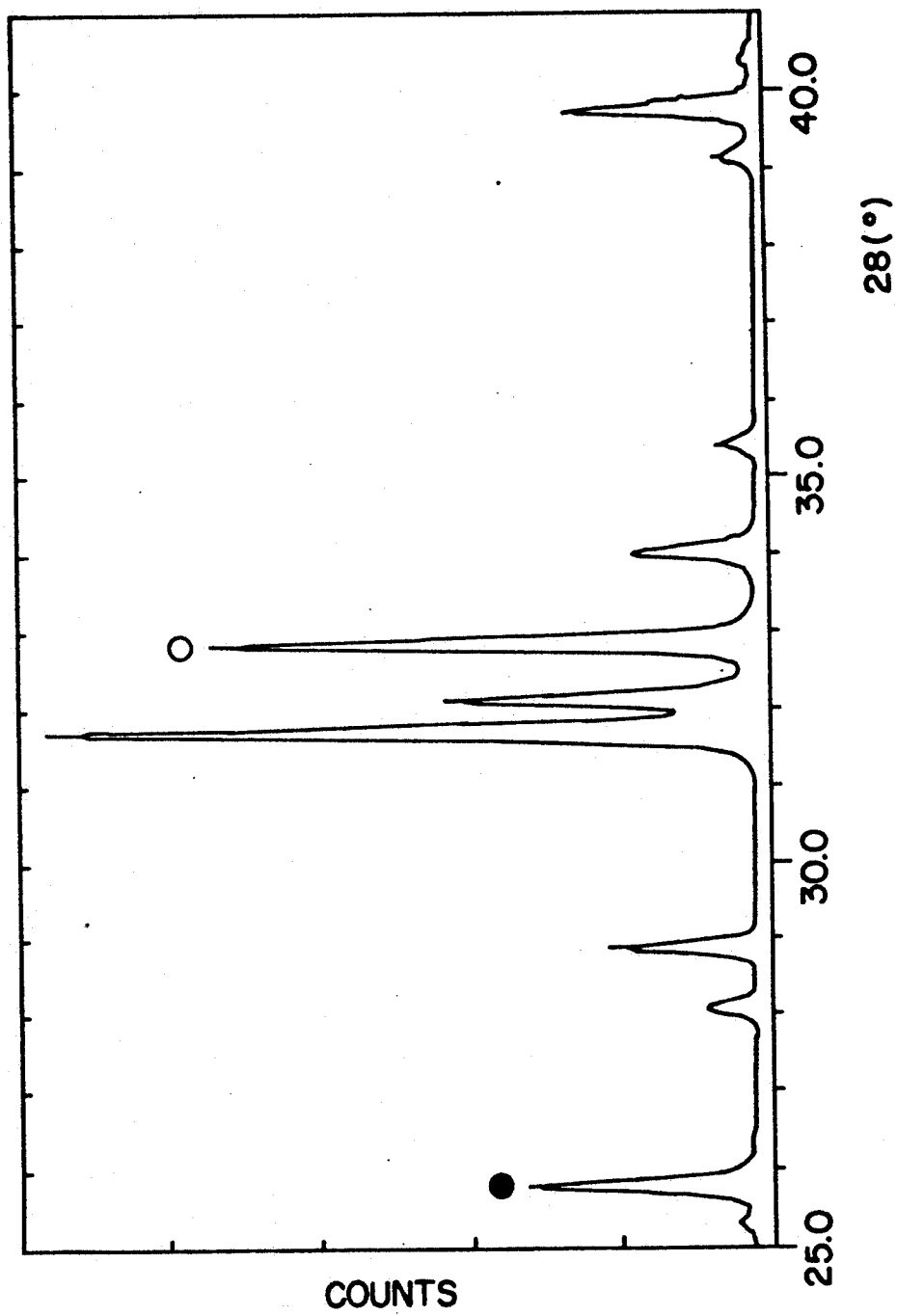
FIG. 6 is an X-ray diffraction scan for the shaped article prepared in Example 3 after it was pulverized.

The result of X-ray diffractiometry on the shaped article is shown in FIG. 5 and the result of an X-ray diffractiometry for the pulverized product of the article is shown in FIG. 6. As is clear from these scans and from the data shown in Table 1, the shaped article produced in Example 3 had grain orientation as in Example 1.

TABLE 1

| Sample | | Degree of orientation |
|---|---|---|
| Example 1 | shaped article | 3.02 |
| Example 1 | pulverized product | 0.05 |
| Example 2 | shaped article | 1.94 |
| Example 2 | pulverized product | 0.15 |
| Example 3 | shaped article | 10.52 |
| Example 3 | pulverized product | 0.51 |

COMPARATIVE EXAMPLE 1

A sinter was produced in the same manner as in Example 1 except that the powder synthesized, dried and calcined as in Example 1 was immediately used without being pulverized by jet milling. X-ray diffraction analysis of the surface of the sinter showed no grain orientation. This would be because the diameter of the secondary particles in the powder was so large that precluded the orientation of primary particles during shaping.

COMPARATIVE EXAMPLE 2

A sinter was produced in the same manner as in Example 2 except that shaping was performed with a cubic mold in place of the plate mold. X-ray diffraction analysis of the surface of the sinter showed no grain orientation. This would be because a mold having a larger cross section than the length of the final shaped article caused the injected composition to diffuse without having the grains oriented.

EXAMPLE 4

Figure 7:
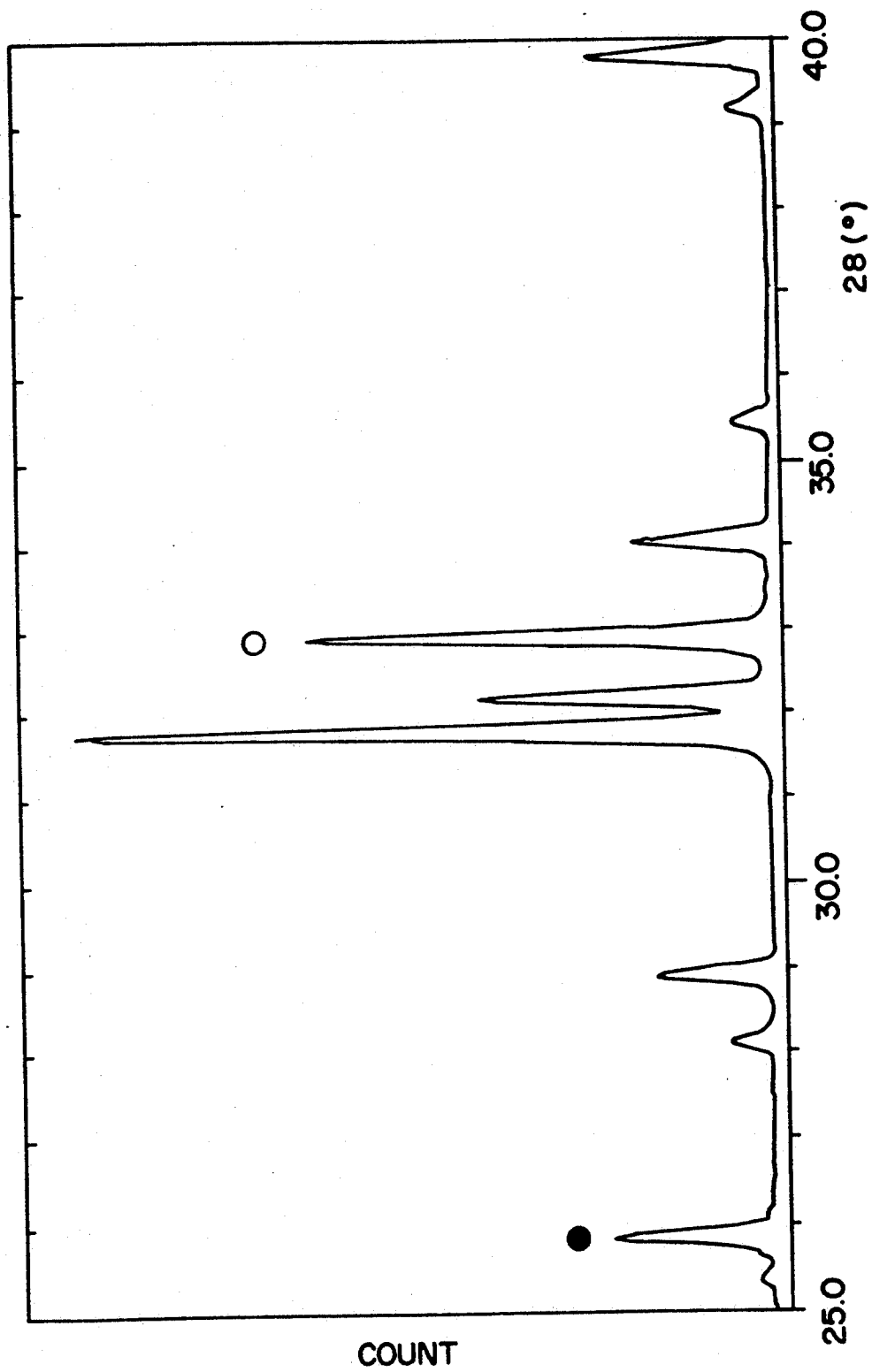
FIG. 7 is an X-ray diffraction scan for the plane parallel to the molding direction of the shaped article prepared in Example 4.

An hydroxyapatite cylinderical molded article, which was molded, dried and degreased in the same manner as in Example 1, was fired at 1,100° C. to obtain a sinter. The sinter was cut in the direction parallel to the molding direction or in the direction perpendicular to the molding direction. The cut surfaces were polished and measured for X-ray diffraction scans. The X-ray diffraction scan for the cut surface parallel to the molding direction is shown in FIG. 7. The X-ray diffraction scan for the cut surface perpendicular to the molding direction is shown in FIG. 8. Separately, the sinter was pulverized in a mortar and measured for an X-ray diffraction scan which is shown in FIG. 9.

From the diffraction intensity for the (300) face ($I_{(300)}$) which is parallel to the c axis and the diffraction intensity for the (002) face ($I_{(002)}$) which is perpendicular to the o axis, it was found that the ratios of $I_{(300)}/I_{(002)}$ were 2.87, 1.03 and 1.67 for FIGS. 7, 8 and 9, respectively.

It is understood from the above results that the a axis of the primary particles of this sinter was oriented in the direction perpendicular to the molding direction, and the c axis was oriented in the direction parallel to the molding direction.

EXAMPLE 5

An hydroxyapatite plate-like molded article, which was molded, dried and degreased in the same manner as in Example 4, was fired at 1,100° C. to obtain a sinter. From the measurement of X-ray diffraction scans, it was found that the sinter had the same orientation properties as in the sinter obtained in Example 4.

The sinter was cut into a dimension of 3×4×40 mm, and the cut surfaces were mirror-polished followed by annealing at 1,050° C. for 2 hours in the air. The cut direction was determined such that the longitudinal direction of the cut specimen became parallel or perpendicular to the molding direction. The specimen in which the longitudinal direction is parallel to the molding direction was designated Sample A, and the specimen in which the longitudinal direction is perpendicular to the molding direction was designated Sample B.

Samples A and B were measured for the following mechanical properties.

(1) Hardness

The hardness was measured by the Vickers method at a load of 300 g. The penetrator was penetrated in the face parallel to the orientation direction in Sample A, and in the face perpendicular to the orientation direction in Sample B.

(2) Fracture toughness ($K_{1C}$)

The breaking toughness ($K_{1C}$) was measured by the IM method and Niihara's equation using the dents formed upon measuring the hardness.

(3) Bending strength

The bending strength was measured by the three-points method according to JIS R1601.

(4) Modulus of elasticity

The modulus of elasticity was measured by a bending load method using a strain gauge.

The results obtained are shown in Table 2 below. The values in Table 2 are the average values and 95% confidence intervals for 10 specimens.

TABLE 2

| Sample | Hardness (GPa) | Fracture toughness (MPam$^{\frac{1}{2}}$) | Bending strength (MPa) | Modulus of elasticity (GPa) |
|---|---|---|---|---|
| A | 5.0 ± 0.4 | 0.74 ± 0.05 | 99.8 ± 21.9 | 114.3 ± 6.4 |
| B | 4.6 ± 0.2 | 0.63 ± 0.05 | 85.2 ± 11.0 | 121.9 ± 8.1 |

It was found from the variance analysis of the results in Table 2 that significant differences between Samples A and B was 95% for hardness and 99% for fracture toughness. Therefore, the sinters of the present invention have anisotropy for mechanical properties.

In accordance with the present invention, a certain crystallographic axis of the primary particles in at least the surface or the entire portion of the shaped article to be produced can be oriented in one direction by a simple method. The shaped article of a calcium phosphate calcium compound or the sinter thereof which is produced by the present invention has grain orientation so that their mechanical, electrical and chemical properties are sufficiently anisotropic to provide improved characteristics over conventional materials. Further, the shaped article and sinter thereof are improved in fracture toughness.

While the invention has been described in detail and with reference to specific embodiments thereof, it will be apparent to one skilled in the art that various changes and modifications can be made therein without departing from the spirit and scope thereof.

What is claimed is:

1. A process for producing an oriented shaped article of a calcium phosphate compound, which process comprises: mixing an organic binder and water or an organic solvent with a powder of a calcium phosphate compound comprising rod-shaped crystal grains extending in the direction of one crystallographic axis thereof, kneading the mixed components, and extruding the resulting composition in a specified direction to shape said composition.

2. The process of claim 1, wherein at least two crystallographic axes of primary particles of which said oriented shaped article is composed each is oriented in one direction, respectively, in at least the surface of said article.

3. The process of claim 2, wherein said at least two crystallographic axes of the primary particles of which said oriented shaped article is composed each is oriented in one direction, respectively, in the entire portion of said article.

4. The process of claim 1, wherein the calcium phosphate compound is hydroxyapatite.

5. The process of claim 1, where the extruding is extrusion molding at a molding pressure of from 0.2 to 500 kg/cm$^2$.

6. The process of claim 1, wherein the extruding is injection molding at a molding pressure of from 500 to 3,000 kg/cm$^2$.

7. The process of claim 1, wherein the composition which is extruded comprises hydroxyapatite, water, butyl alcohol, methyl cellulose, a wax emulsion and a stearic acid emulsion.

8. The process of claim 1, wherein the composition which is extruded comprises hydroxyapatite, butyl methacrylate, an ethylene-vinyl acetate copolymer, a wax emulsion, dibutyl phthalate and stearic acid.

9. A process for producing an oriented sinter of a calcium phosphate compound, which process comprises: mixing an organic binder and water or an organic solvent with powder of the calcium phosphate compound comprising rod-shaped crystal grains extending in the direction of one crystallographic axis thereof, kneading the mixed components, extruding the resulting composition in a specified direction to shape said composition, thermally decomposing the organic binder, and firing the shaped article at a temperature of from 900° to 1,400° C.

10. The process of claim 9, wherein at least two crystallographic axes of primary particles of which said oriented shaped sinter is composed each is oriented in one direction, respectively, in at least the surface of said sinter.

11. The process of claim 10, wherein said at least two crystallographic axes of the primary particles of which said oriented shaped sinter is composed each is oriented in one direction, respectively, in the entire portion of said sinter.

12. The process of claim 9, wherein the calcium phosphate compound is hydroxyapatite.

13. The process of claim 9, where the extruding is extrusion molding at a molding pressure of from 0.2 to 500 kg/cm$^2$.

14. The process of claim 9, wherein the extruding is injection molding at a molding pressure of rom 500 to 3,000 kg/cm$^2$.

15. The process of claim 9, wherein the composition which is extruded comprises hydroxyapatite, water, butyl alcohol, methyl cellulose, a wax emulsion and a stearic acid emulsion.

16. The process of claim 9, wherein the composition which is extruded comprises hydroxyapatite, butyl methacrylate, an ethylene-vinyl acetate copolymer, a wax emulsion, dibutyl phthalate and stearic acid.

* * * * *

UNITED STATES PATENT AND TRADEMARK OFFICE
CERTIFICATE OF CORRECTION

PATENT NO. : 5,240,659

DATED : August 31, 1993

INVENTOR(S) : Takeshi Ichitsuka, et al.

It is certified that error appears in the above-indentified patent and that said Letters Patent is hereby corrected as shown below:

On the title page item [73],
Delete the name of the Assignee as shown therein,
i.e., "Asahi Kogaku K.K." and insert therefor
--Asahi Kogaku Kogyo K.K.--

Signed and Sealed this

Thirty-first Day of October 1995

Attest:

BRUCE LEHMAN

*Attesting Officer*   *Commissioner of Patents and Trademarks*